(12) United States Patent
Zhou et al.

(10) Patent No.: US 11,285,107 B2
(45) Date of Patent: Mar. 29, 2022

(54) PROCESS FOR MANUFACTURING POROUS SILICA PARTICLES LOADED WITH AT LEAST ONE BIOACTIVE COMPOUND ADAPTED FOR LUNG, NASAL, SUBLINGUAL, AND/OR PHARYNGEAL DELIVERY

(71) Applicant: Nanologica AB, Södertälje (SE)

(72) Inventors: Chunfang Zhou, Stockholm (SE); Adam Feiler, Hässelby (SE); Paulina Paszkiewicz, Stockholm (SE); Xin Xia, Bandhagen (SE)

(73) Assignee: NANOLOGICA AB, Södertälje (SE)

( * ) Notice: Subject to any disclaimer, the term of this patent is extended or adjusted under 35 U.S.C. 154(b) by 0 days.

(21) Appl. No.: 16/609,854

(22) PCT Filed: May 3, 2018

(86) PCT No.: PCT/EP2018/061436
§ 371 (c)(1),
(2) Date: Oct. 31, 2019

(87) PCT Pub. No.: WO2018/202818
PCT Pub. Date: Nov. 8, 2018

(65) Prior Publication Data
US 2020/0069588 A1    Mar. 5, 2020

(30) Foreign Application Priority Data
May 4, 2017   (SE) .................................... 1750544-7

(51) Int. Cl.
*A61K 9/14*    (2006.01)
*A61K 9/00*    (2006.01)

(52) U.S. Cl.
CPC ............ *A61K 9/143* (2013.01); *A61K 9/0075* (2013.01)

(58) Field of Classification Search
None
See application file for complete search history.

(56) References Cited

U.S. PATENT DOCUMENTS

| | | | |
|---|---|---|---|
| 6,254,854 B1 | 7/2001 | Edwards et al. | |
| 6,740,310 B2 | 5/2004 | Edwards et al. | |
| 2015/0209285 A1* | 7/2015 | Van Speybroek | ... A61K 9/1611 424/452 |
| 2015/0224077 A1 | 8/2015 | Gerhart et al. | |
| 2019/0038553 A1* | 2/2019 | Engqvist | .............. A61K 31/485 |

FOREIGN PATENT DOCUMENTS

| | | |
|---|---|---|
| EP | 3618811 B1 | 9/2020 |
| GB | 2355711 A | 5/2001 |
| WO | 2003011251 A1 | 2/2003 |
| WO | 2008150537 A2 | 12/2008 |
| WO | 2009010770 A2 | 1/2009 |
| WO | 2009101110 A2 | 8/2009 |
| WO | 2016/054225 | 4/2016 |
| WO | 2016054225 A1 | 4/2016 |
| WO | 2017023407 A2 | 2/2017 |

OTHER PUBLICATIONS

Shetl et al. "Factors influencing aerodynamic particle size distribution of suspension pressurized metered dose inhalers" 2015.*
Van Holsbeke et al. Median mass aerodynamic diameter (MMAD) and fine particle faction (FPF): Influence on lung deposition? 2014. https://erj.ersjournals.com/content/44/Suppl_58/P912.*
Van Holsbeke et al. Median mass aerodynamic diameter (MMAD) and fine particle faction (FPF): Influence on lung deposition? 2014.*
Carvalo et al. "Influence of particle size on regional lung deposition-what evidence is there?", 2011.*
Sheth et al. "Factors influencing aerodynamic particle size distribution of suspension pressurized metered dose inhalers" 2015.*
Mohsnei et al. "Preparation and Characterization of Rifampin Loaded Mesoporous silica Nanoparticles as a Potential System for Pulmonary Delivery" 2015.*
Mohseni et al. "Preparation and In-vitro Evaluation of Rifampin-loaded Mesoporous Silica Nanoaggregates by an Experimental Design" 2015.*
Kwon et al. "Silica-based mesoporous nanoparticles for controlled drug delivery" 2013.*
Shapiro "Air Classification of Solid particles: a review" 2003.*
International Search Report dated Jul. 18, 2018 in International Patent Application No. PCT/EP2018/061436.
International Preliminary Report on Patentability dated Jul. 24, 2019 in International Patent Application No. PCT/EP2018/061436.
Written Opinion of the International Searching Authority dated Jul. 18, 2018 in International Patent Application No. PCT/EP2018/061436.
Written Opinion of the International Examining Authority dated Mar. 25, 2019 in International Patent Application No. PCT/EP2018/061436.
Gradon, et al., "Formation of particles for dry powder inhalers", Advanced Powder Technology, Oct. 2013, pp. 43-55, vol. 25, issue 1.
Schüepp, et al., "Deposition of Aerosols in Infants and Children," Journals of Aerosol Medicine, Jun. 2004, pp. 153-156, vol. 17, issue 2.
Shapiro, et al., "Air classification of solid particles: a review," Chemical Engineering and Processing, 2005, pp. 279-285, vol. 44, issue 2.

(Continued)

*Primary Examiner* — Danah Al-Awadi
(74) *Attorney, Agent, or Firm* — Kim IP Law Group LLC (57) ABSTRACT

The present invention relates to a process for manufacturing porous silica particles comprising at least one bioactive compound, whereby the particles are adapted for lung, nasal, sublingual and/or pharyngeal delivery of said at least one bioactive compound and have an MMAD between 0.5 and 15 μm with a GSD less than 2.5. The invention also relates to a pharmaceutical composition comprising said silica particles and a use of the silica particles in the diagnoses, prevention and/or treatment of local and/or systemic disorders, such as disorders of the lung, nose, sublingual and/or pharynx.

19 Claims, 5 Drawing Sheets

(56) References Cited

OTHER PUBLICATIONS

Clemens, et al., "Targeted Intracellular Delivery of Antituberculosis Drugs to *Mycobacterium tuberculosis*-infected Macrophages via Functionalized Mesoporous Silica Nanoparticles," Antimicrobial Agents and Chemotherapy, May 2012, pp. 2535-2545, vol. 56, issue 5.

Li, et al., "Aerosol droplet delivery of mesoporous silica nanoparticles: A strategy for respiratory-based therapeutics," Nanomedicine: Nanotechnology, Biology, and Medicine, Aug. 2015, pp. 1377-1385, vol. 11, issue 6.

Parikh, et al., "Improved Localized Lung Delivery Using Smart Combination Respiratory Medicines," European Respiratory Disease, 2012, pp. 40-45, vol. 8, issue 1.

Taratula, et al., "Innovative strategy for treatment of lung cancer: targeted nanotechnology-based inhalation co-delivery of anticancer drugs and siRNA," Journal of Drug Targeting, 2011, pp. 900-914, vol. 19, issue 10.

Feiler, "Nanoporous Silica—an unexploited technology pöatformed for delivery of biologics?", Jun. 13, 2016, DDF Summit, San Diego.

Australian Examination Report dated Aug. 12, 2020 in Australian Patent Application No. 2018262708.

Communication under Rule 71(3)EPC—Intention to Grant dated Jun. 3, 2020 in European Application No. 18723453.9.

Chinese Office Apr. 23, 2021 in Chinese Patent Application No. 201880029084.8.

Indian Examination Report dated Apr. 8, 2021 in Indian Patent Application No. 201947044302.

Chinese Office Action dated Aug. 3, 2021 in Chinese Patent Application No. 201880029084.8.

Office Action in Chinese Patent Application No. 201880029084.8, dated Nov. 3, 2021.

Office Action in Japanese Patent Application No. 2019-560246 with a Drafting Date of Oct. 26, 2021 and dated Nov. 2, 2021.

* cited by examiner

Figure 1:
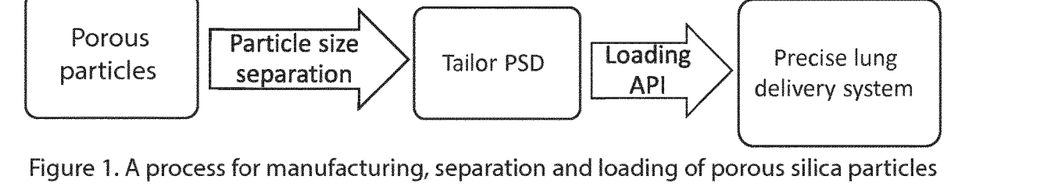

Figure 1. A process for manufacturing, separation and loading of porous silica particles Figure 2. Particles size distribution determination with Marple Cascade Impactor of NLAB Silica before and after air classification.

Figure 3:
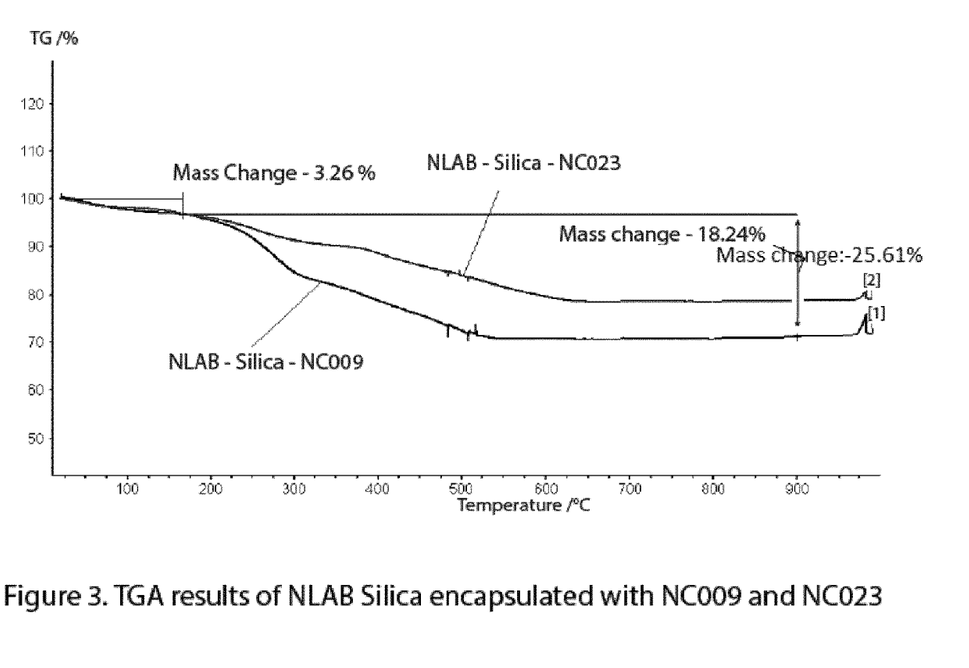

Figure 3. TGA results of NLAB Silica encapsulated with NC009 and NC023

Figure 4:
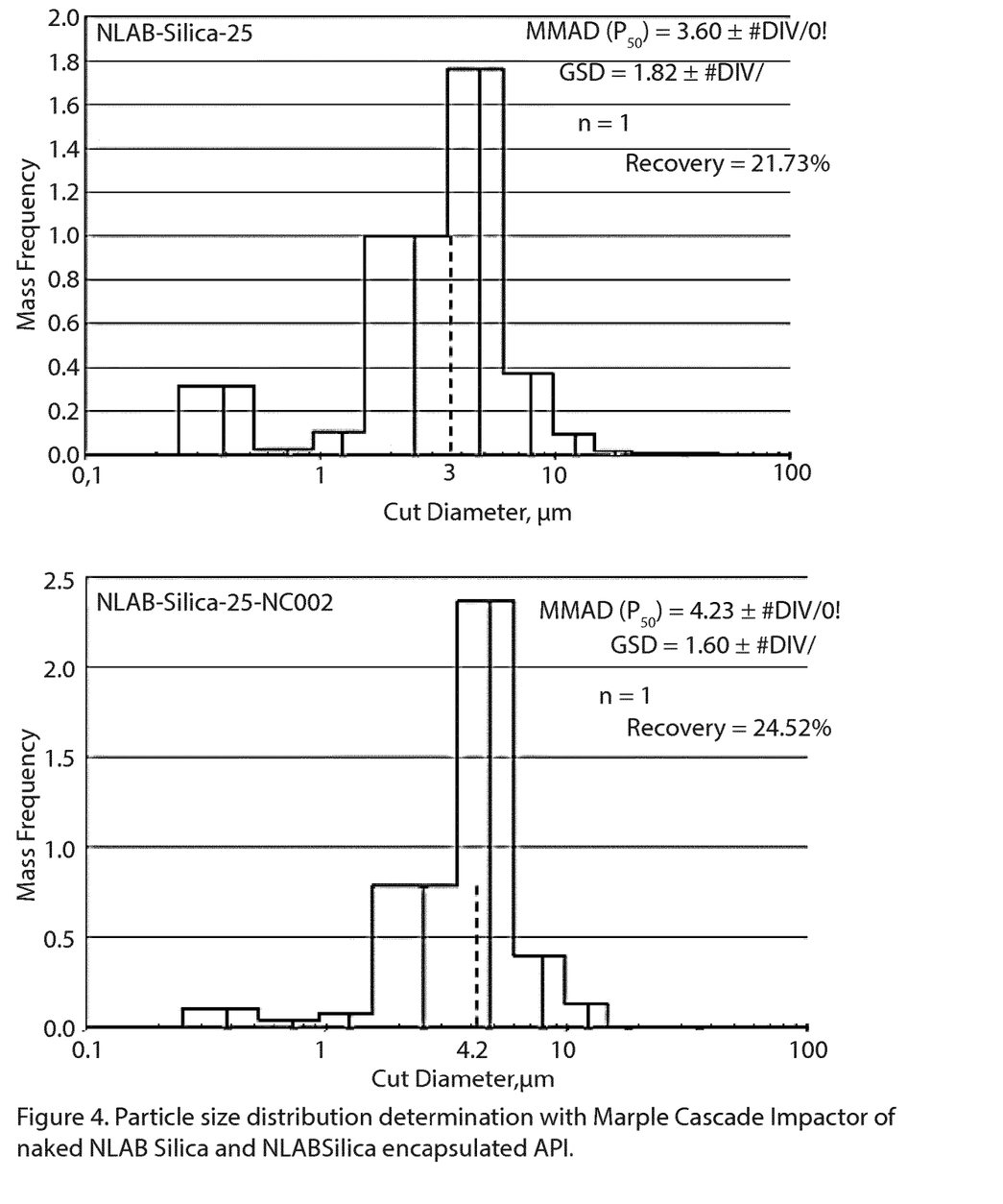

Figure 4. Particle size distribution determination with Marple Cascade Impactor of naked NLAB Silica and NLABSilica encapsulated API.

Figure 5:
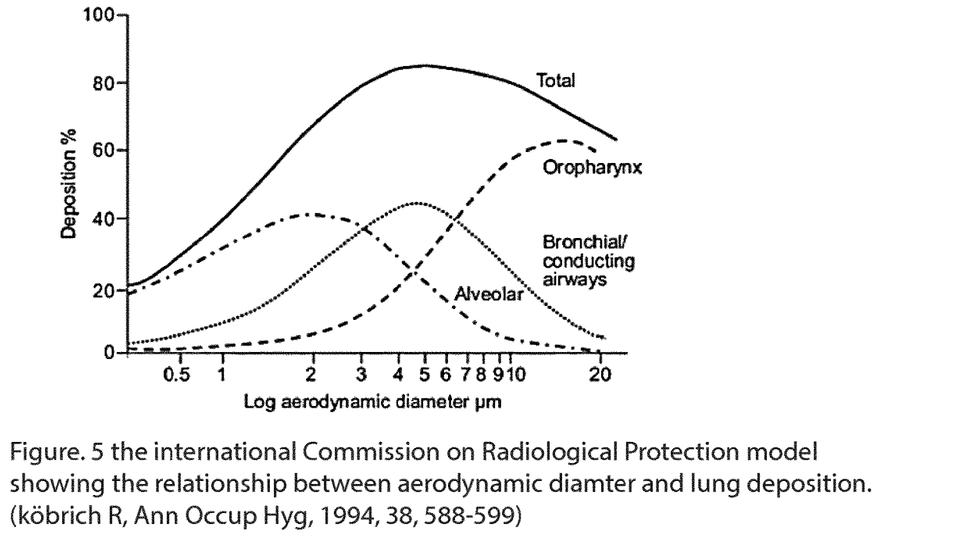

Figure. 5 the international Commission on Radiological Protection model showing the relationship between aerodynamic diamter and lung deposition. (köbrich R, Ann Occup Hyg, 1994, 38, 588-599)

Figure 6:
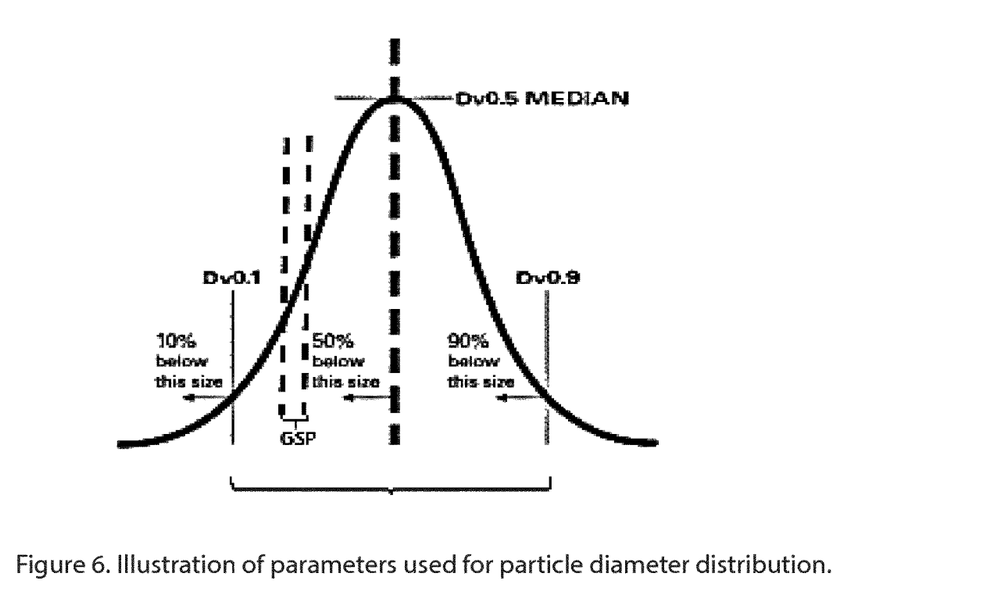

Figure 6. Illustration of parameters used for particle diameter distribution.

Figure 7:
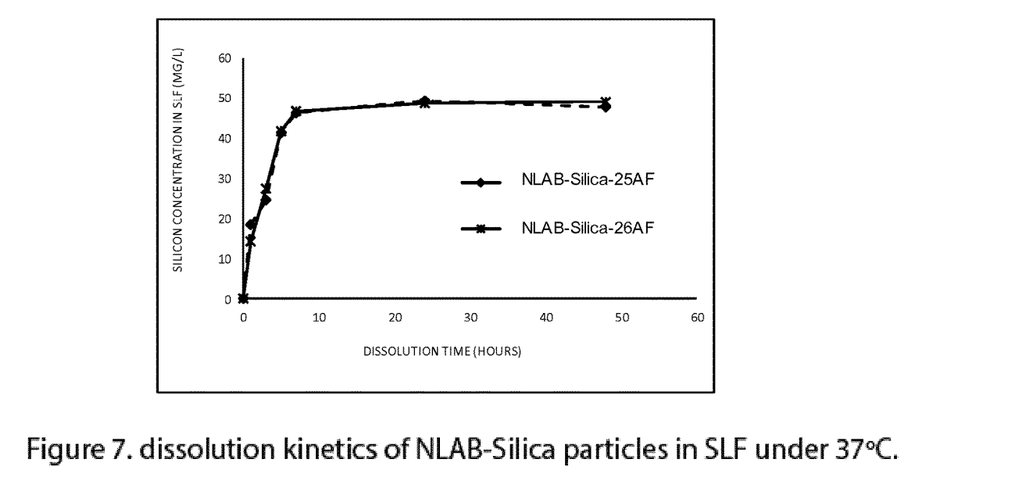

Figure 7. dissolution kinetics of NLAB-Silica particles in SLF under 37°C.

Figure 8:
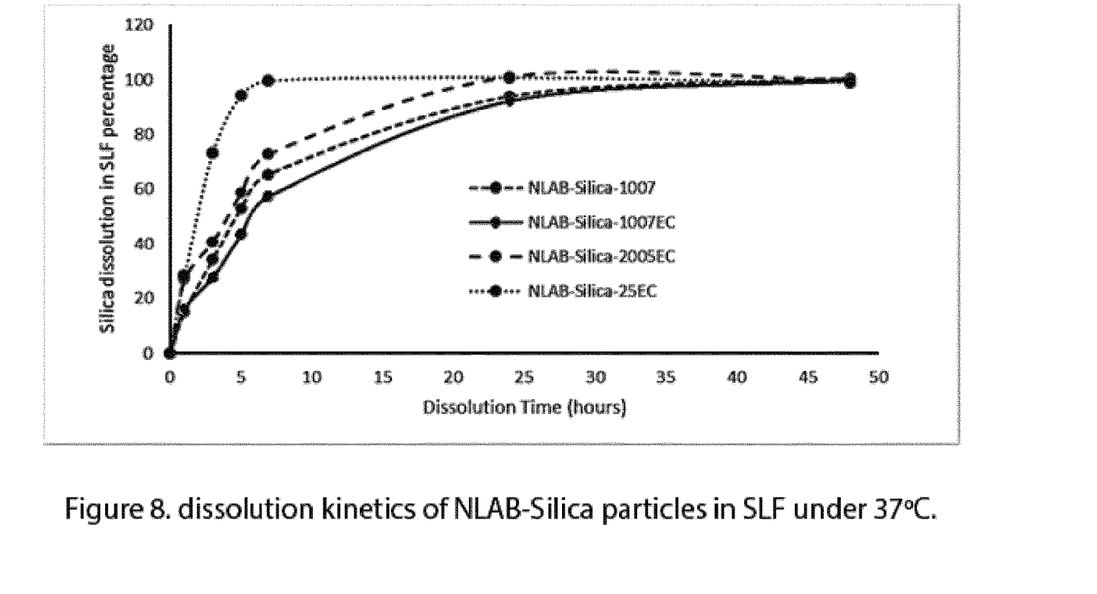

Figure 8. dissolution kinetics of NLAB-Silica particles in SLF under 37°C.

PROCESS FOR MANUFACTURING POROUS SILICA PARTICLES LOADED WITH AT LEAST ONE BIOACTIVE COMPOUND ADAPTED FOR LUNG, NASAL, SUBLINGUAL, AND/OR PHARYNGEAL DELIVERY

CROSS-REFERENCE TO RELATED APPLICATIONS

This application is a U.S. national phase application under 35 U.S.C. § 371 of International Application No. PCT/EP2018/061436, filed on May 3, 2018, which claims priority to Swedish Patent Application No. 1750544-7, filed May 4, 2017, the disclosure of which is hereby incorporated by reference in its entirety fo all purposes.

FIELD OF THE INVENTION

The present invention relates to a process for manufacturing porous silica particles comprising at least one bioactive compound, whereby the particles are adapted for lung, nasal, sublingual and/or pharyngeal delivery of said at least one bioactive compound. The invention also relates to a pharmaceutical composition comprising said silica particles and a use of the silica particles in the diagnoses, prevention and/or treatment of local and/or systemic disorders, such as disorders of the lung, nose, sublingual and/or pharynx.

BACKGROUND OF THE INVENTION

Administration of bioactive compounds or drugs to the lungs is challenging and complicated. The compounds need to be formulated in a composition suitable for use in an inhalation device and suitable for inhalation.

The pharmaceutical composition is preferably biocompatible, biodegradable and soluble. The particle size or diameter in the composition must be below 6 µm in order to reach the lower lung. Disaggregation and dispersion of the drug upon exiting an inhalation device is important for delivery of the drug to the lung. Particles larger than 6 µm do not enter the lower lung, i.e. the bronchi and alveoli. Particles larger than 6 µm are suitable for drug delivery in the upper lung, throat or nose.

Comparing with traditional drug delivery systems, the inhaled drug delivery system presents much more difficulties in understanding various aspects of drug deposition pattern and absorption of the drug via the lungs due to the complexity of the respiratory system. For therapeutic efficacy, inhaled drug compositions must efficiently deposit in the airway and be available to produce therapeutic action locally or efficiently traverse the air-blood barrier to produce systemic effects. In the upper lung, the epithelia of the lung comprise a periciliary layer of cells with a luminal mucus layer on top of the cell layer. Any bioactive compound will need to traverse the mucus layer to get into the cell layer. In the alveoli in the lower lung, the cell layer is in an aqueous phase and covered by pulmonary surfactant. A bioactive compound needs to traverse the surfactant layer to get to the cell layer underneath. The mucus layer and the surfactant layer are composed of different materials and thus permeation through these layers requires different properties. Therefore, the site of deposition is expected to influence the rate and extent of absorption of a bioactive compound in the lung. Compounds having a solubility of 10 µM or more in water are easier absorbed in the upper lung, while solubility of a bioactive compound is less important in the lower lung. However, peak systemic exposure is reduced in the lower lung, when the solubility of a compound is below 10 µM.

The deposition of inhaled particles is strongly influenced by a number of parameters that include mass median aerodynamic diameter (MMAD), density and shape of particles and hygroscopicity of particles. A widely-accepted notion is that for efficient deposition, the MMAD should be in the range of 1 and 5 µm. Smaller sized particles are likely to be exhaled and larger sized particles are deposited in the upper airways. Preferably, monodispersed particles are used having a narrow particle size distribution.

Dissolution of bioactive compounds in the mucus or surfactant layer is important for therapeutic effect. Compounds having low solubility and/or a low dissociation constant are less effective in the lung because of low drug exposure. In some cases, low solubility of compounds can be used to the advantage of prolonging the drug action because the retention time in the lung is longer. In case of pulmonary disorders, the epithelia of the lung may be different and a rate limiting step for therapeutic effect of a bioactive compound may change from dissolution rate of a compound to permeation rate of the compound through the air-blood barrier. Deposition of a compound in the different regions of the lungs is also affected by disorders. In case of asthma, more drug is deposited in the upper lung compared to healthy volunteers. When less drug is deposited in the lower lung, less drug is permeated through the air-blood barrier in the alveoli and this in turn reduces the systemic effect of the drug.

Suitable pharmaceutical compositions for pulmonary delivery have preferably controlled particle size and sharp and controllable particle size distribution (PSD), which is beneficial for precise lung deposition. Particle size influences the deposition of particles in the different areas in the lung. In current compositions, particles are made from the pharmaceutical composition itself, which typically includes the bioactive compound in crystalline form together with other additives or excipients. The particle size influences the dissolution rate of the compound from the particle or crystal. For example, it takes longer for pharmaceutically bioactive compounds to dissolve from larger particles than from smaller ones.

The composition is preferably not sensitive to humidity because that may cause the composition to aggregate and affect the deposition pattern of particles.

Suitable pharmaceutical composition for pulmonary delivery of drugs or bioactive compounds are dry powder compositions. Such compositions are often limited to the use of crystalline drugs, because oily or amorphous compounds are extremely difficult to formulate into a dry powder that can be used for consistent and invariable dosing.

Porous particles have been developed to improve the delivery of bioactive compounds to the lungs, such as improved controlled release of the bioactive compound, improved control on particles size, improved loading of the drug in the particle composition, etc.. The delivery of bioactive compound may be locally, systemic and in an immediately or extended release form.

U.S. Pat. No. 6,740,310 discloses dry powder composition for deep lung delivery of a bioactive compound, which comprises spray dried porous or non-porous particles, whereby 55% of the particles have an aerodynamic diameter (MMAD) less than 4.7 µm and a mass density less than 0.1 g/cm$^3$.

U.S. Pat. No. 6,254,854 discloses a dry composition comprising biodegradable particles for delivery of a bioactive compound in the deep lung, whereby the particles are made of a polyester copolymer and have a mass median diameter (MMD) between 5 and 30 μm and a mass median aerodynamic diameter (MMAD) between 1 and 5 μm with a mass density less than 0.4 $g/cm^3$.

The parameters of the particles are controlled by the manufacturing and separation processes. Important parameters are mass median diameter (MMD) and mass median aerodynamic diameter (MMAD). Particles produced in a manufacturing process often have a wide range in diameters, whereby the distribution of the range follows a Gauss curve (see FIG. 6). The parameter used to define the distribution of MMAD is the geometric standard deviation $(D_{84.1}/D_{15.9})^{1/2}$ (GSD). FIG. 5 shows the relation between aerodynamic diameter (MMAD) and lung deposition. It is shown that particles with a size of 4-5 μm deposit primarily in the bronchia, whereas smaller particles (about <4 μm) remain in the airstream and are carried into the peripheral airways and the alveolar region of the lower lung. Another parameter used to define particles is mass density and fine particle fraction (FPF). The FPF is the proportion of particles that have a diameter below 5 μm. Other parameters of the particle that are important are surface area, shape of the particle and pore volume of the particle.

Selection of particles within a desired range is commonly done by separating particles that are loaded with a bioactive compound, using e.g. filters to obtain particles within a desired range, such as 55% having a diameter less than 4.7 μm.

Tartula O, et al., J. Drug Targeting, 2017, 19(10, p 900-914, discloses a strategy for treating lung cancer using nanotechnology, whereby silica particles are prepared using a surfactant-template method. The particles are manufactured in a uniform size of 160 nm+/−75. After loading the average size is 200 nm +/−100. The surface of the particles is firstly conjugated with pyridylthiol, where after the particles are loaded with DOX or CIS. Subsequently, the pyridylthiol conjugate is replaced by an iRNA and LHRH conjugate. This manufacturing process is specific for the bioactive compounds used and is time consuming and expensive.

WO2003/011251 discloses loaded particles prepared by etching, filtering or grinding to obtain microparticles of porous silicon particles of monodispersed size and shape. It is mentioned that the particles may be loaded with biologically active material either before or after the grinding process. No example is disclosed of loaded particles having a narrow size distribution. Unfortunately, it has since the publication of this application, been known that silicon may cause serious adverse effects in the lung.

US2015224077 discloses a method for preparation of particles using nebulization. It is mentioned that porous particles may be used but no examples are disclosed of the preparation of loaded porous particles.

GB2355711 discloses a method for the preparation of particles, whereby the particles are sized during the manufacturing of the particles. Sizing is preferably done by sieving because the use of an air classifier is expensive. However, it is mentioned that both methods of sizing cannot be used to obtain highly purified porous silica particles.

WO2008150537 discloses a preparation method of porous silica particles for use in chromatography. The particles may be sized prior to use. Loading of particles is not mentioned nor is any separation of size of the particles mentioned prior to loading with a bioactive compound.

Inhalation devices may be metered dose inhalers (MDI), dry powder inhalers (DPI) and soft mist inhalers (SMI). DPIs are most widely used and these may be divided into low, medium and high resistant DPIs. The pharmaceutical compositions used in these devices often comprise additives such as propellants, surfactants, antioxidants, humidity regulators and the like.

The efficiency of these devices is affected by two main forces 1) an inspiration air flow (IAF), which depends on a flow generated by the patient, and 2) a turbulence produced by the device. A balance between these two forces is important for optimal performance of a device. If the IAF is too high, most of the drug is lost in the upper lung, i.e. the throat and the trachea. If the IAF is too low, more drug is delivered in the lower lung, this is the bronchi and alveoli, but with low disaggregation and dispersion of the drug. Mostly used are DPIs with medium resistance because these devices are less dependent on IAF for disaggregation and dispersion of the composition in the lung.

Other technologies for inhalation compositions have been developed. Compositions of fixed-dose drug combinations must ensure powder homogeneity and delivery of a uniform dose to the patients, particularly when the ratio of each drug present in the formulation significantly differs. In an attempt to reach these requirements and achieve co-deposition of drugs in the lungs, particle engineering has been used instead of a simple blending of micronized drugs with coarse carrier particles. Pearl Therapeutics (California, USA) has used a process to prepare a triple fixed-dose combination formulation. First, an emulsion of DSPC (1.2-distearoyl-sn-glycero-3-phosphocholine) and anhydrous calcium chloride are spray dried to form porous microparticles. Subsequently, the porous particles and micronized glycopyrrolate, formoterol fumarate, and mometasone furoate were co-suspended in 1.1.1.2-tetrafluorothane (HFA) pro pellant. The drug microparticles adhere irreversibly to the porous particle surfaces, forming a stable suspension with equivalency in dose delivered for each drug.

Another attempt to prepare a homogeneous composition of a triple fixed-dose combination was reported by Parikh D, Burns J, Hipkiss D, Usmani O, et al. Improved localized lung delivery using smart combination respiratory medicines. European Respiratory Disease. 2012;8(1):40-5. The solution atomization and crystallization method (SAXTM) is a method that involves the formation of drug concentrated droplets followed by sono-crysta treatment with ultrasound waves to create cavitation bubbles for fast nucleation and crystallization. This process produces a powder formulation with appropriate dose-delivery homogeneity and aerodynamic properties.

Other micronization methods have been used. The disadvantage of these micronized powders is that the dissolution rate of the drug is dependent on the particle size of the powder and the characteristics of the drug, such as solubility. Delivery of bioactive compounds thus still depends on the IAF and the turbulence produced by the delivery device.

The shape of the particles is important for flow kinetics of the particles and for the deposition and dissolution of the bioactive compound comprised in the particles. It is difficult to manufacture spherical or pseudo-spherical, cylindric particles in micromillimeter size, i.e. particles having a diameter of more than 2 μm, or between 1 and 50 μm.

OBJECT AND SUMMARY OF THE INVENTION

It is an object of the present invention to at least partly overcome the above problems, and to provide an improved process for manufacturing porous silica particles loaded with or comprising at least one bioactive compound, whereby the particles are adapted for sublingual, lung, nasal and/or pharyngeal delivery of said at least one bioactive compound.

This object is achieved by a process for manufacturing loaded porous silica particles comprising at least one bioactive compound, comprising or consisting of the steps of
- provide the silica particles,
- separating the particles to obtain particles having an MMAD between 0.5 and 15 μm with a GSD less than 2.5,
- loading the obtained particles with at least one bioactive compound, and
- optionally loading the particles with an additional bioactive compound.

In one aspect, the particles have an MMAD between 0.5 and 5 μm with a GSD less than 2.5, or an MMAD between 5 and 15 μm with a GSD less than 2.5.

In an aspect, the particles have an MMAD between 0.5 and 3.5 μm with a GSD less than 1.5.

In another aspect, the particles have an MMAD between 6 and 12 μm, or between 8 and 12 μm, with a GSD less than 2.

The process allows for separation of the particles prior to attaching or loading of a bioactive compound. Alternatively, the bioactive compound may be manufactured as nanocrystals and adsorbed onto a silica particle. The process improves the yield and efficiency of the manufacturing process. This reduces manufacturing costs compared to processes, whereby separation is done after attaching the particles to a bioactive compound. Higher amounts of the bioactive compound can be present in the final composition.

Another advantage is that the process can be used independent of the morphology of the compound. Crystalline, oily and amorphous compounds can be attached to or loaded in the particles and used in the process of the invention. This also allows for preparation of particles that can be delivered locally or systemically and improves flexibility of treatment of any disease. It improves flexibility of treatment of airway disorders, such as disorders of the lung, nose and pharynx. Dissolution of the compound from the particles is independent of the morphology of the compound and independent of the site of delivery of the compound. the dissolution is improved in the lower lung as well as in the upper lung, because the compound dissolute from the particles in both the luminal mucus layer as well as the surfactant layer.

The process allows for control of parameters of the particles that are important for delivery of bioactive compounds, such as MMAD and GSD. As explained above, these parameters are different for delivery of the particles (and bioactive compound) to the lower lung, compared to delivery to the upper lung or throat (including the sublingual cavity under the tongue) or nasal cavity. The process allows for selection of a narrow size distribution of particles with a GSD of less than 4, or 2.5, or 1.5 prior to loading of or attaching a bioactive compound to the particles. This improves monodispersion of the particles size and thus enables controlling the site of deposition of the particles in the lung. Also, homogeneity of the composition comprising the particles can be improved.

Further, more than one bioactive compound can be loaded into and/or attached to the particles without any substantially loss of material. This further reduces costs for manufacturing of the particles. The process is relatively simple compared to the processes known in the art.

In one aspect, the invention relates to a process for manufacturing porous silica particles comprising at least one bioactive compound, comprising or consisting of the steps of
- providing the silica particles,
- separating the particles to obtain particles having an MMAD between 0.5 and 15 μm with a GSD less than 2.5.

Thus, the process may be used for delivery of empty porous particles. These particles may be useful in the treatment of diseases, such as diabetes, obesity and may reduce cholesterol, especially LDL, in the blood.

The outer surface of the amorphous silica may be such that aggregation of the particles is minimized. Reduced aggregation of the particles reduces dependency on inspiration air flow (IAF) and turbulence produced by the inhalation device. This improves the balance between the two forces as discussed above, and thus improves efficiency of delivery of bioactive compounds in the lower lung without loss of bioactive compound in the upper lung. Aggregation may depend on the bioactive compound loaded in or attached to the particle. Aggregation may be prevented by use of a specific bioactive compound.

In another aspect, the process comprises or consists of a further step of surface modifying the particles prior to separation or prior to loading. On one aspect, surface modifying is done prior to separation. On a further aspect, surface modifying is done prior to loading. Surface modifying, such as chemically surface modifying, e.g. etching, results in an altered surface of the silica particles. This may be useful to prevent to particles from aggregating. This is especially useful when the particles have a size of 10 or 6 μm or less. Surface modifying particles prior to loading does not seem to have an influence on the dissolution rate of the bioactive compound from the particles.

In a further aspect, the process comprises or consists of a further step of surface modifying the particles by coating after manufacturing or after loading. In one aspect, coating is done after manufacturing. In a further aspect, coating is done after loading. Coating may be used to adhere a bioactive compound to the surface of the particles. Coating may be used to provide an electrical charge on the surface of the particle and thereby preventing aggregation of the particles. This is especially useful when the particles have a size of 10 or 6 μm or less. In one aspect, the particles are coated with a functionalizing agent. In an aspect, the particles are coated with a surfactant. In another aspect, the particles are coated with an amino acid selected from the group comprising or consisting of L-lysine, L-alanine, glycine, leucine and L-tyrosine. Coating may be done to block the pores in the particle or coating may be done without blocking the pores of the particle.

In another aspect, the process comprises or consists of a further step of surface modifying the particles prior to separating or prior to loading, whereby surface modifying is chemically surface modifying, such as etching and coating, such as non-blocking of pores coating.

The particles may be manufactured by any process known in the art. In one aspect, the particles are manufactured by reacting tetraethyl orthosilicate with a template made of micellar structures. Tetraethyl orthosilicate may also be used with an additional polymer as a template. In another aspect, the particles are manufactured by a sol-gel method, such as the Stober process, or by a spray drying method. In a further aspect, silica particles are manufactured by a sol-gel method comprising a condensation reaction of a silica precursor solution with a non-miscible organic solution, oil, or liquid polymer in which droplets are formed by stirring or spraying the solution followed by gelation of the silica by means of change in pH and/or evaporation of the aqueous phase. The sol-gel method has an advantage over other methods in that it is less cumbersome, less costly and adapted for large scale production of silica particles under Good Manufacturing Practice (GMP).

In one aspect, the silica particles are nano-porous and/or meso-porous silica particles. In another aspect, the particles are nanoporous silica particles. In an aspect, the particles are mesoporous silica particles. In a further aspect, the silica particles are spheres, pseudo-spheres, cylindrical, gyroids, rods, fibers, core-shell shaped of particles. In a further aspect, silica particles are spherical or cylindrical. This may improve flow kinetics of the particles. The shape of the particles can be controlled by the manufacturing process. This may be important for the deposition and dissolution of the bioactive compound.

In an aspect, the silica particles are biodegradable. In one aspect, the silica particles are dissolvable. In one aspect, the particles are biodegradable and dissolvable. In a further aspect, the silica is synthetic amorphous silica. For some applications it is an advantage if the silica is biocompatible, dissolvable and biodegradable. This may reduce possible toxic effects of the particles in the lung, nose and throat, especially in the deeper lung.

In another aspect, the silica particles have a pore size between 1 and 100 nm. In yet another aspect, the silica particles have a pore volume between 0.1 and 3 $cm^3/g$. In a further aspect, the silica particles have a surface area between 40 and 1200 $m^2/g$. Measurements were done by nitrogen adsorption isotherm and calculated using BET (Brunauer-Emmett-Teller) model to calculate the pore volume and pore size. In another aspect, he silica particles may have a pore size between 1 and 100 nm, a pore volume between 0.1 and 3 $cm^3/g$ and a surface area between 40 and 500 $m^2/g$.

The particles may be separated by any process known in the art. In one aspect, the particles are separated using an air classifier, or cyclonic separation, or elutriation, or sedimentation and/or sieving using one or more sieves. In a further aspect, the particles are separated using an air classifier.

The particles may be loaded by any process known in the art. In one aspect, the particles are loaded using solvent evaporation, impregnation, spray-drying, melting, supercritical $CO_2$ loading or freeze-drying. In a further aspect, the particles are loaded using solvent evaporation. The term "loading" means that the bioactive compound may be loaded into and/or onto the particle, or otherwise be attached to the particle. An advantage of loading compounds into porous silica particles is that dissolution rate of the compound is influenced by the pore structure, such as pore volume rather than the size of the silica particle. This results in dissolution kinetics of the compound that is independent of particle size. Particle size is the key parameter determining deposition of the particles in the lung. Therefore, dissolution kinetics of the compound can be tailored and be independent of the position of the particles in the lung. By using silica porous particles, the dissolution of the compound from the particles is independent of the morphology of the compound and independent on the site of delivery. With the method of the invention, a composition can be obtained, whereby the delivery of a bioactive compound is less or not dependent on the morphology of the compound, or less or not dependent on turbulence caused by the delivery device, or less or not dependent on the inspiration airflow generated by the patient as compared to known compositions.

In an aspect, the silica particles are manufactured using a sol-gel method, silica particles are separated using an air classifier and the particles are loaded using solvent evaporation.

In a further aspect, the particles have a fine particle fraction of at least 90%, or 99%, or 99.8%.

For delivery of a bioactive compound in the deeper lung, the particles have an MMAD of 6 µm, or 3 µm, or between 0.5 and 5 µm, or between 1 and 3.5 µm, with a GSD less than 2.5, or 2.2, or 2.0, or 1.8, or 1.5.

For delivery of a bioactive compound in the sublingual, nasal and/or pharyngeal cavity, the particles have an MMAD of at least 5, or 10 µm, or between 5 and 15 µm, or between or between 6 and 12 µm, or between 8 and 12 µm, or between 7.5 and 11.5 µm with a GSD less than 4, or 2.5, or 2, or 1.5. In another aspect, the GSD is between 1 and 2. An advantage of the process of the invention is that "monodispersed" particles with a narrow range distribution (i.e. low MMAD and narrow GSD) can be obtained. This means that the site of deposition of the particles in the lung can be tailored with improved accuracy compared to prior art particles. For example, more particles and thus more bioactive compound can be delivered in the deep lung. This also improves the homogeneity of the composition comprising the particles.

In yet another aspect, the particles have a mass density less than 0.4 $g/cm^3$, or between 0.15 and 0.35 $g/cm^3$. In yet a further aspect, the particles have a fine particle fraction (FPF) is at least 75%, 80%, 85%, 90%, 95%, 98%, 99% or 99.9%, or 100%. In one aspect, the FPF is between 98 and 100%, or between 99 and 100%, or between 99.5 and 100%. The MMD or MMAD can be varied depending on the site of delivery of the bioactive compound. Thus, for lower lung delivery the MMAD may be below 3 or 6 µm, while for nasal delivery the MMAD may be 10 µm or more. The GSD may be the same for both the lower lung and nasal delivery. Alternatively, a dosage having more than one selected MMAD may be used, such as a dosage having 50% of particles with an MMAD of 1 to 3 µm with a GSD between 1 and 1.5, and 50% of particles having an MMAD of 10 µm or more with a GSD between 1 and 2.

The invention also relates to a pharmaceutical composition adapted for lung delivery of bioactive compounds, comprising or consists of a plurality of porous silica particles loaded to 0.1 to 80%, or 5 to 50% of the total weight of the loaded particles, with at least one bioactive compound, and optionally other pharmaceutical excipients, diluents or additives, and optionally coated with a functionalizing agent, characterized in that the particles have an MMAD between 0.5 and 5 µm with a GSD less than 2.5. In one aspect, the particles have an MMAD between 0.5 and 3.5 µm with a GSD less than 1.5. In another aspect, the particles have been prepared according the process for manufacturing as defined above.

The invention also relates to a pharmaceutical composition adapted for sublingual, nasal and/or pharyngeal delivery of bioactive compounds, comprising or consists of a plurality of porous silica particles loaded to 0.1 to 80%, or 5 to 50*% of the total weight of the loaded particles, with at least one bioactive compound, and optionally other pharmaceutical excipients, diluents or additives, characterized in that the particles have an MMAD between 5 and 15 µm with a GSD less than 2.5. In one aspect, the particles have an MMAD between 8 and 12 µm with a GSD less than 2. In another aspect, the particles have been prepared according the process for manufacturing as defined above.

The pharmaceutical composition can be used for local and/or systemic delivery of one or more bioactive compounds.

The pharmaceutical composition can be used for immediate release and/or extended release of one or more bioactive compounds. When more than one bioactive compound is present in or on the particles in the composition, one bioactive may be delivered locally, while a second bioactive can have a systemic effect. Also, the different bioactive compound may be released from the particles at different rates.

In yet another aspect, the bioactive compound is a crystalline, or an amorphous or an oily compound. In an aspect, the bioactive compound is an amorphous compound. The composition of the invention can deliver a consistent/uniform drug dose, which is independent of solubility of the bioactive compound. In other words, the dissolution rate is not influenced by the morphology of the bioactive compound. When a therapeutic use of a compound no longer depends on the morphological form or solubility of the compound, many more bioactive compounds can be developed, which improves development of new drugs and flexibility in diagnoses and treatment of a patient. Even in combination therapy, the homogeneity of the dose is ensured and a uniform dose of more than one bioactive compounds can be administered to a patient.

In another aspect, the bioactive compound has a water solubility at 25° C. of 10 mg/ml or more according to Ph.Eur $9^{th}$ Ed. An example of the bioactive compound may be metoclopramide, which has a solubility of 10 mg/ml in buffer at pH 6.8 and >6 mg/ml in water.

In yet another aspect, the bioactive compound has a water solubility at 25° C. of 1 to 10 mg/ml according to Ph.Eur $9^{th}$ Ed.. In an aspect, the bioactive compound has a water solubility at 25° C. below 1 mg/ml according to Ph.Eur $9^{th}$ Ed.. Porous particles may enhance dissolution kinetics of poorly water-soluble bioactive compounds, i.e. bioactive compounds having a water solubility at 25° C. below 10 mg/ml. An example of the bioactive compound may be Clofazimine, which has a solubility of 0.225 mg/l or OSU-03012 (insoluble in water) or folic acid, which has a solubility of 1.6 mg/l.

By using the particles, a larger amount of bioactive compound can be delivered at the site of delivery compared to known compositions. This means that the frequency of dosing can be reduced and thus effectiveness and efficiency of treatment as well as costs for health care are reduced. The silica particles are compatible with most additives and can be blended with other additives without much problem. But, fewer additives are needed in the composition of the present invention, which reduces costs for manufacturing of the composition. Further, silica, especially amorphous silica, is less sensitive to humidity compared to the dry crystalline powder composition as used in inhalers today. This reduces the risk for aggregation of the particles, which in turn reduces the dependency on IAF and turbulence in the device by using the particles manufactured according to the process of the invention. The loading capacity of the particles is increased compared to prior art particles. Also, loading of the bioactive compound into the (nano)porous silica provides the compound in a stable amorphous state, which enhances dissolution kinetics and controlled release. The particles have an improved homogeneity even when the particles comprise more than one bioactive compound.

An improved efficiency of deposition of the bioactive compound in the lung allows for more precise lung delivery and thus an improved therapeutic effect of the compound both locally and systemically. The exposure of the bioactive compound to the lung, pharynx or nose is increased. Further, the silica particles allow for delivery of higher dose to a specific site.

In another aspect, the bioactive compound is selected from the group comprising or consisting of antiallergics, bronchodilators, pulmonary lung surfactants, analgesics, antibiotics, antiinfectives, leukotriene inhibitors or antagonists, antihistamines, antiinflammatories, antineoplastics, anticancer, anticholinergics, anaesthetics, antituberculars, cardiovascular agents, enzymes, steroids, genetic material, viral vectors, antisense agents, proteins, peptides and combinations thereof. In one aspect, the bioactive compound is a protein or peptide, such as a tripeptide, growth factors or oligonucleotides.

In a further aspect, the bioactive compound is selected from the group comprising or consisting of Gefitinib, Dasatinib, Imatinib, Bosutinib, Diclofenac (Sodium), Felodipine, Indapamide, Itraconazole and Quetiapine.

In an aspect, the bioactive compound is selected from the group comprising or consisting of Clofazimine (NC009), OSU-03021 (N023) and folic acid (NC026).

The invention further relates to a delivery device adapted for lung, nasal, sublingual and/or pharynx delivery of at least one pharmaceutical bioactive compound comprising or consisting of the pharmaceutical composition as defined above, optionally mixed with a propellant. In one aspect, the propellant is selected from the group comprising or consisting of hydrocarbon, fluorocarbon, hydrogen-containing fluorocarbon or mixtures thereof having a sufficient vapour pressure to efficiently form aerosols upon activation of a metered dose inhaler. In an aspect, the pharmaceutical composition does not comprise or consist of a propellant. The composition of the invention reduces the need for co-development of inhalation devices. The delivery device may be a metered dose inhalers (MDI), a dry powder inhaler (DPI) or a soft mist inhalers (SMI). The delivery device may be a dry powder inhaler (DPI), especially a DPI with medium resistance. This delivery device further reduces the dependence of delivery of the compound on the IAF and the turbulence of the device for disaggregation and dispersion of the compound in the lung.

In a metered dose inhaler, the pharmaceutical composition is present in a liquid form, as a solution or suspension. It can be challenging to prevent dissolution of a bioactive compound from the particle or to prevent leakage of the compound from the particle. Typically, solvents or surfactants are chosen to keep a suspension of drug particles stable. Typically, the compound has low solubility in the solvents used. Stable compound suspensions can be prepared by loading compounds into silica particles. Silica particles are well dispersed in different solvents and may be further modified to prevent dissolution or leakage of drug into the solvent before delivery to the target site or lung, e.g. by coating the particles. An advantage of loading into silica is that a large range of compounds can be formulated as a drug suspension. Further, silica particles have a high drug load capacity, whereas most formulations have limited compound/drug concentrations per particle. Furthermore, compounds of any morphology can be loaded in the particles and used in the device.

The invention further relates to diagnostic, preventive and/or therapeutic use of the pharmaceutical composition as defined above. In one aspect, the pharmaceutical composition as defined above may be used for diagnoses, prevention and/or treatment of a local and/or systemic disorder of the lung, nose, sublingual cavity or pharynx selected from the group comprising or consisting of infection, inflammation, COPD, asthma, cancer, tuberculosis, severe acute respiratory syndrome, respiratory syncytial virus, influenza, small pox and drug resistant respiratory infection. One aspect related to diagnoses, prevention and/or treatment of a local and/or systemic disorder of the lung selected from the group comprising or consisting of infection, inflammation, COPD, asthma, cancer, tuberculosis, severe acute respiratory syndrome, respiratory syncytial virus, influenza, small pox and drug resistant respiratory infection. One aspect related to diagnoses, prevention and/or treatment of a local and/or systemic disorder of the lung wherein the disorder is cancer and the compound is selected from Gefitinib, Dasatinib, Imatinib, Bosutinib.

The invention related to a dry powder device adapted for lung, nasal, sublingual and/or pharynx administration of a pharmaceutical composition comprising or consisting of a plurality of porous particles loaded with at least one bioactive compound, optionally mixed with a propellant, and optionally other pharmaceutical excipients, diluents or additives, wherein the particles have been manufactured by
  providing the porous particles, preferably by manufacturing by a sol-gel method or by a spray drying method, whereby the particles have a pore size between 1 and 100 nm, a pore volume between 0.1 and 3 cm$^3$/g and a surface area between 40 and 1200 m$^2$/g,
  and the particles are pseudo-spherical or cylindrical,
  separating the particles prior to loading, preferably by using an air classifier, or cyclonic separation, or elutriation, or sedimentation and/or sieving, more preferably by using an air classifier,
    to obtain particles having an MMAD between 0.5 and 15 µm with a GSD less than 2.5, and a FPF of at least 99.0%,
  loading the particles with at least one bioactive compound, preferably by solvent evaporation, impregnation, spray-drying, melting, supercritical $CO_2$ loading or freeze-drying, more preferably solvent evaporation,
  - whereby the porous silica particles are loaded with 5% w/w or more with at least one bioactive compound,
- optionally modifying the surface of the particles, preferably by etching and/or coating, preferably without blocking the pores,
- optionally loading the particles with an additional bioactive compound,
  - whereby a concentration of the porous silica particles in the pharmaceutical composition is 5% w/w or more based on the total weight of the pharmaceutical composition.

The bioactive compound may be selected from the group comprising or consisting of Gefitinib, Dasatinib, Imatinib, Bosutinib, Diclofenac (Sodium), Felodipine, Indapamide, Itraconazole, Quetiapine, Clofazimine (NC009), OSU-03021 (N023) and folic acid (NC026).

Any interval of a feature may be replaced by another interval of the same feature as mentioned in the description.

BRIEF DESCRIPTION OF THE DRAWINGS

The invention will now be explained more closely by the description of different aspects of the invention and with reference to the appended figures.

FIG. 1 shows a flow diagram of a process for manufacturing, separating and loading of porous silica particles.

FIG. 2 shows particle size distribution determination with Marple Cascade Impactor of NLAB-Silica before and after air classification.

FIG. 3 shows TGA results of NLAB Silica encapsulated with NC009 and NC023 as bioactive compounds.

FIG. 4 shows particle size distribution determination with Marple Cascade Impactor of naked NLAB Silica and NLAB Silica encapsulated bioactive compound.

FIG. 5 shows the International Commission on Radiological Protection model showing the relationship between aerodynamic diameter and lung deposition. (Köbrich R, Ann Occup Hyg, 1994, 38, 588-599)

FIG. 6 Illustrates parameters used for particle diameter distribution.

FIG. 7 shows dissolution kinetics of NLAB-Silica particles in SLF under 37° C.

FIG. 8 shows dissolution kinetics of NLAB-Silica particles having different pore structure in SLF under 37° C.

DETAILED DESCRIPTION OF PREFERRED ASPECTS OF THE INVENTION

Definitions and Measurement Methods

As used herein, a "bioactive compound" means a pharmaceutical (bio)active compound having a preventive, prophylaxis or treating effect in/on a mammal body, such as a human. A bioactive compound may be a biological active compound such as a protein, peptide, antibody and the like.

As used herein, the term "disease" is intended to include disorder, condition or any equivalent thereof.

The term "loading" means that the bioactive compound may be loaded into and/or onto the particle, or otherwise be attached to the particle.

The term "extended release" means any release of a bioactive compound that is not immediate, i.e. not a release of at least 80% of the compound within 30 minutes.

As used herein, the term "patient" refers to a mammal, for example, a human.

As used herein, the term "substantially" or "about" refers to a deviation of a value around the number mentioned, e.g. substantially or about 5 means that the value may be between 4 and 6.

As used herein, the term "coating" refers to coverage of a surface, which may include blockage of the pores or not.

As used herein, the term "surface modifying" refers to a modification, change in the physical and/or chemical properties of the surface.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

As used herein, the term "optional" or "optionally" means that the subsequently described event or circumstance may but need not occur, and that the description includes instances where the event or circumstance occurs and instances where it does not.

As used herein, the term "compound" refers to a natural or synthetic compound as well as any natural or synthetic biologic compound, such as peptides, growth factors, oligonucleotides and the like.

NC009 means Clofazimine, N,5-bis(4-chlorophenyl)-3-propan-2-yliminophenazin-2-amine, CAS 2030-63-9, N023 means OSU-03021 2-amino-N-(4-(5-(phenanthren-2-yl)-3-

(trifluoromethyl)-1H-pyrazol-1-yl)phenyl)acetamide, CAS 742112-33-0, and NC026 means folic acid, N-(4-{[(2-amino-4-oxo-1,4-dihydropteridin-6-yl)methyl]amino}benzoyl)-L-glutamic acid, CAS 59-30-3.

Mercury (Hg) intrusion is a standard method for measuring porosity. In this method mercury is pushed into pores under applied pressure. However, there is a lower pore size limit of around 3.2 nm, below which, the mercury cannot penetrate. For porous materials with pore sizes in the mesoscale range of 1 to 50 nm, nitrogen ($N_2$) sorption is commonly used to estimate pore size and pore volumes. The nitrogen sorption technique measures the available surface area of the porous materials. An empirical model is used to calculate the pore volume and pore size. The BET (Brunauer-Emmett-Teller) and BJH (Barrett, Joyner and Halenda) models are used to calculate porosity for the pores of silica particles.

Scanning electron microscope (SEM) can be used to provide images of the porous particles. The diameter of the particles can be determined using SEM.

Porous particles may be manufactured by cooperative self-assembly of silica species and organic templates, such as cationic surfactants, such as alkyltrimethylammonium templates with varying carbon chain lengths, and counterions,, such as cetyltrimethylammonium chloride (CTA+Cl− or CTAC) or cetyltrimethylammonium bromide (CTA+Br− or CTAB) or non-ionic species, such as diblock and triblock polymer species, such as copolymers of Polyethylene Oxide and Polypropylene Oxide, for example Pluronic 123 surfactant. The formation of mesoporous silica particles occurs following the hydrolysis and condensation of silica precursor, which can include alkylsilicates such as tetraethylorthosilcate TEOS or teramethylorthosilicate TMOS in solution or sodium silicate solution. The mesoporous silica particle size can be controlled by adding suitable additive agents, e.g. inorganic bases, alcohols including methanol, ethanol, propanol and organic solvents, such as acetone, which affect the hydrolysis and condensation of silica species. The pore size can be influenced by hydrothermal treatment of the reaction mixture, such as heating up to 100° C. or even above and also with the additional of swelling agents in the form of organic oils and liquids that expand the surfactant micelle template. After condensation of the silica matrix, the templating surfactant can be removed by calcination, typically at temperatures from 500° C. up to 650° C. for several hours which burns away the organic template resulting in a porous matrix of silica. The template may alternatively be removed by extraction and washing with suitable solvents, such as organic solvents or acidic of basic solutions.

The porous silica particles may be manufactured by a sol-gel method comprising a condensation reaction of a silica precursor solution, such as sodium silicate or an aqueous suspension of silica nanoparticles as an emulsion, with a non-miscible organic solution, oil, or liquid polymer in which droplets are formed by for example stirring or spraying the solution followed by gelation of the silica by means of change in pH and/or evaporation of the aqueous phase. The porosity of the particles here are formed either by exclusion due to the presence of the non-miscible secondary phase or by the jamming of the silica nanoparticles during evaporation. The particles may further be treated by heating to induce condensation of the silica matrix and washing to remove the non-miscible secondary phase. Furthermore, the particles may be treated by calcination to strengthen the silica matrix.

The porous particles may be manufactured as porous glass through a process of phase separation in borosilicate glasses (such as $SiO_2$—$B_2O_3$—$Na_2O$), followed by liquid extraction of one of the formed phases through the sol-gel process; or simply by sintering glass powder. During a thermal treatment, typically between 500° C. and 760° C., an interpenetration structure is generated, which results from a spinodal decomposition of the sodium-rich borate phase and the silica phase.

The porous particles may be manufactures using fumed process. In this method, fumed silica is produced by burning silicon tetrachloride in an oxygen-hydrogen flame producing microscopic droplets of molten silica, which fuse into amorphous silica particles in three-dimensional secondary particles, which then agglomerate into tertiary particles. The resulting powder has an extremely low bulk density and high surface area.

FIG. 1 shows a flow diagram of a process of the invention for manufacturing porous silica particles loaded with or comprising at least one bioactive compound. The term "loading" means that the bioactive compound may be loaded into and/or onto the particle, or otherwise attached to the particle. The particles obtained are adapted for lung, nasal, sublingual and/or pharyngeal delivery of said at least one bioactive compound. The process comprises or consists of the step as outlined below.

In a first step, the silica particles are provided. The invention is not limited to a specific manufacturing method. Examples of manufacturing method are disclosed in WO2009/101110. Other methods are mentioned above.

In a second step, the particles are separated to obtain particles having an MMAD between 0.5 and 15 μm with a GSD less than 2.5.

Separating may be done by using an air classifier. An air classifier is an industrial machine, which separates particles by a combination of size, shape, and density. It works by feeding the raw particles to be sorted into a chamber, which contains a column of rising air. Inside the separation chamber, air drag on the particles supplies an upward force, which counteracts the force of gravity and lifts the particles to be sorted up into the air. Due to the dependence of air drag on particle size and shape, the particles in the moving air column are sorted vertically and can be separated in this manner. Examples of suitable air classifiers may be a Stage Non Viable Cascade Impactor, a Marple Miller Impactor or a Multi-stage Liquid Impinger.

Separation may also be done by air classifier, or cyclonic separation, or elutriation, or sedimentation and/or sieving using one or more sieves.

In a third step, the particles obtained in step two are loaded with or attached to at least one bioactive compound. More than one bioactive compound may be loaded as well. The particles can also be functionalized by use of biomarkers like fluorophore, contrast or radioactive agents that may be attached to or loaded on/into the particles.

The particles may be loaded using different techniques, such as solvent evaporation, impregnation, spray-drying, melting, supercritical $CO_2$ loading or freeze-drying, and the like. Solvent evaporation involves combining a concentrated solution of the bioactive compound with the silica particles, then removing the solvent and/or drying the sample prior to further processing.

The loading of the porous silica particles may be about 5% w/w or more, or about 15%, 20%, 25%, 30%, 40%, 50%, 75%, 80%, 85%, 90%.

Optionally, a second or subsequent loading step is performed. This may be done to increase the loading of the one or more bioactive compound in step 3, or this may be done to load the particles obtained in step 3 with a second or subsequent bioactive compound. The different bioactive compound may be in admixture with the porous particles and/or the different bioactive compound may be loaded in and/or loaded on in the porous particles. The invention is not limited to any combination hereof.

The process may comprise or consist of a further step of surface modification of the particles prior to separating of prior to loading. Surface modification is preferably done prior to loading. Surface modification may be a chemical modification, such as etching. Etching may be done by boiling the silica particles in a base, and then in an acid to form —S—OH bonds on the outer surface of the particle. Examples of suitable bases may be a solution of KOH, n-propanol in water, a solution of NaOH or $N_2CO_3$ and ammonia, or $NaBH_4$, or HF. Examples of suitable acids may be HCl and $H_2SO_4$.

The process may comprise or consist of a further step of coating the particles after manufacturing or after loading. Coating is preferably done prior to loading. Preferably, the pores are not blocked by the coating. At least a portion of the total particles may be coated. The coating may be a taste-masking coating or an mucoadhesive coating. The coating may also be used to improve hydrophilicity or lipophilicity. The coating may even be used to charge the particles on the surface.

Suitable coating agents may be a functionalizing agent selected from the group comprising or consisting of amino acids, surfactant, polymer, lipids, cellulose or derivatives thereof, saccharides, stearates like magnesium stearate, peptides, proteins and nanoparticles, which may be porous. Examples of amino acids may be L-lysine, L-alanine, glycine, leucine and L-tyrosine.

The silica particles may be nanoporous or mesoporous, or a mixture thereof. The silica particles may have a pore size between 1 and 100 nm, or between 1 and 80 nm, or between 2 and 50 nm, or between 2 and 25 nm, or between 5 and 15 nm, or substantially 12 nm.

The silica particles may have a pore volume between 0.1 and 3 $cm^3/g$, or between 0.2 and 2 $cm^3/g$, or between 0.5 and 1.5 $cm^3/g$, or between 0.7 and 1.2 $cm^3/g$, or between 0.5 and 1.0 $cm^3/g$ substantially 8.5 $cm^3/g$.

The silica particles may have a surface area between 40 and 1200 $m^2/g$, or between 60 and 1100 $m^2/g$, or between 100 and 1000 $m^2/g$, or between 50 and 800 $m^2/g$, or between 50 and 600 $m^2/g$. The particles as used in the description may have any combination of the intervals mentioned above. For example, the silica particles may have a pore size between 2 and 100 nm, a pore volume between 0.1 and 3 $cm^3/g$ and a surface area between 100 and 1000 $m^2/g$. The silica particles may have a pore size between 2 and 50 nm, a pore volume between 0.5 and 1.5 $cm^3/g$ and a surface area between 50 and 800 $m^2/g$.

The silica particles may have different shapes. The shapes of the particles can be controlled by the process and may be spheres, pseudo-spheres, cylinders, gyroids, rods, fibres, core-shell shape of particles, or mixtures thereof. The silica particles may be substantially spherical or pseudo-spheres.

The silica may be any silica. The silica may be biodegradable and/or dissolvable. Examples of silica is amorphous silica or synthetic amorphous silica.

The provided particles may have an MMAD between 0.5 and 15 μm. For delivery of a bioactive compound in the deep lung, the particles may have an MMAD between 0.5 and 5 μm, or between 0.5 and 3.5, or 0.6 and 4, or 0.75 and 3.5, or 1 and 3 μm with a GSD less than 2.5, or 2.2, or 2.0, or 1.8, or 1.5, or 1.2, and a FPF of at least 99.5%.

For delivery of a bioactive compound in the upper long, nose, sublingual or throat, the particles may have an MMAD of at least 5 μm, or between 0.1 and 15 μm, or between 5 and 12 μm, 6.5 and 8.5, or 7.5 and 9.5, or 8.5 and 10.5, or 9.5 and 11.5 μm, with a GSD less than 2.5, or 2.2, or 2.0, or 1.8, or 1.5, or 1.2, and a FPF of at least 99.0%.

The GSD of the particles, independent on the site of delivery, may be between 0.75 and 4, or between 1 and 2.5, or between 1 and 2, or between 1 and 1.5.

The mass density may be less than 0.4, or between 0.15 and 0.35 $g/cm^3$.

The fine particle fraction (FPF) may be at least 60%, 75%, 80%, 85%, 90%, 95% or 99%. The FPF may be between 95 and 99%, or between 98 and 100%, or between 99.5 and 100%, or between 99.8 and 100%.

The particles obtained in the process of the invention may be used in a pharmaceutical composition adapted for lung, nasal, sublingual and/or pharyngeal delivery of bioactive compounds.

The pharmaceutical composition may comprise or consist of a plurality of porous silica particles loaded between 0.01 and 85%, or 0.05 to 80%, or 0.1 to 70%, or 10 to 60%, or 25 to 58%, whereby the percentage is a percentage of the total weight of the loaded particles, with at least one bioactive compound. As mentioned above, more than one bioactive compound may be loaded in the particles. Alternatively, one or more bioactive compound may be loaded inside the particle or inside and on the surface of particle.

The concentration of the porous silica particles in the pharmaceutical composition may be 5% w/w or more, or 15%, 20%, 25%, 30%, 40%, 50%, 75%, 85%, 90% w/w based on the total weight of the pharmaceutical composition.

For diagnostic purposes, it may be advantageous to use a particle, whereby the signalling or imaging compound is present on or attached to an outer surface of the particles. The imaging compound may be a labelling agent or tracer suitable for imaging in gamma scintigraphy, or single proton emission computed tomography or positron emission tomography (PET), magnetic resonance imaging (MRI) or fluorescence imaging and the like.

The pharmaceutical composition may be used in an inhalation device. The invention is not restricted to any specific inhalation device, which may be a metered dose inhalers (MDI), a dry powder inhaler (DPI) or a soft mist inhaler (SMI). The pharmaceutical composition may be mixed with a propellant inside the inhalation device. The propellant may be selected from the group comprising hydrocarbon, fluorocarbon, hydrogen-containing fluorocarbon or mixtures thereof, having a sufficient vapor pressure to efficiently form aerosols upon activation of a metered dose inhaler. The pharmaceutical composition may be free of or substantially free of propellant.

The composition may further include or consist of other pharmaceutical excipients, diluents or additives. For example, surfactants, wetting agents, bulking agents, adhesion modifiers may be used, such as sugar, lipids, amino acid, surfactant, polymer and absorption enhancer. Suitable pharmaceutical excipients (also called carriers, diluents and additives) may be found in "Pharmaceuticals—The Science of Dosage Form Designs", M. E. Aulton, Churchill Livingstone, 1988. Examples of excipients may be microcrystalline cellulose, such as PH-101, hydroxypropyl cellulose, such as low-substituted, saccharides, such as mannitol, stearates, such as magnesium stearate and cyclodextrins. The pharmaceutical composition may be free of or substantially free of additives.

The pharmaceutical composition for lung delivery of bioactive compounds may comprise a plurality of porous silica particles loaded to 0.1 to 80%, or 5 to 50% of the total weight of the loaded particles, with at least one bioactive compound, and optionally other pharmaceutical excipients, diluents or additives, and optionally surface modified with a functionalizing agent, whereby the particles have an MMAD between 0.5 and 5 μm with a GSD less than 2.5 and a FPF of at least 99.5%. The particles may have an MMAD between 0.5 and 3.5 μm with a GSD less than 1.5, and a FPF of at least 99.8%.

The pharmaceutical composition for sublingual, nasal and/or pharyngeal delivery of bioactive compounds may comprise a plurality of porous silica particles loaded to 0.1 to 80%, or 5 to 50% of the total weight of the loaded particles, with at least one bioactive compound, and optionally other pharmaceutical excipients, diluents or additives, and optionally surface modified with a functionalizing agent, whereby the particles have an MMAD between 5 and 15 μm with a GSD less than 2.5, and a FPF of at least 99.5%. The particles have an MMAD between 8 and 12 μm with a GSD less than 2, and a FPF of at least 99.8%.

The pharmaceutical composition for sublingual delivery of a bioactive compound may comprise or consist of a plurality of porous silica particles loaded between 0.1 and 85%, or 5 to 50% of the total weight of the loaded particles with at least one bioactive compound, whereby the silica particles have an MMAD of at least 5 μm, a GSD less than 2.5 and a FPF of at least 99.5% and additives selected from low-substituted, saccharides, such as mannitol, stearates, such as magnesium stearate and cyclodextrins.

The total amount of bioactive compound in the dosage form may be between 1 and 100 mg, or between 1 and 50 mg, or between 5 and 50 mg, or between 5 and 25 mg.

The dosage form may be administered when needed, or once or twice daily.

The bioactive compound may be a crystalline, or an amorphous or an oily compound. A bioactive compound may exist in both crystalline and amorphous form depending on the solvent, salt, etc. The at least one bioactive compound may have a water solubility at 25° C. of 10 mg/ml or more according to Ph.Eur 9$^{th}$ Ed., or a water solubility at 25° C. of 1 to 10 mg/ml according to Ph. Eur 9$^{th}$ Ed., or a water solubility at 25° C. below 1 mg/ml according to Ph.Eur 9$^{th}$ Ed.. If more than one bioactive compound is used, the water solubility's may be different or the same.

The pharmaceutical composition may be used for diagnosing lung diseases. The composition may also be used for local and/or systemic diagnoses, prevention and/or treatment of a disorder. The disorder may be a disorder of the lung, nose or pharynx. Any lung disorder is included in the application. The disorder (or disease or condition) may be selected from the group comprising or consisting of infection, inflammation, COPD, asthma, cancer, tuberculosis, severe acute respiratory syndrome, respiratory syncytial virus, influenza, small pox and drug resistant respiratory and systemic infection.

The bioactive compound may be selected from the group comprising or consisting of antiallergics, bronchodilators, pulmonary lung surfactants, analgesics, antibiotics, antiinfectives, leukotriene inhibitors or antagonists, antihistamines, antiinflammatories, antineoplastics, anticholinergics, anesthetics, antituberculars, cardiovascular agents, enzymes, steroids, genetic material, viral vectors, antisense agents, proteins, peptides and any combinations thereof. The bioactive compounds may be selected from the group comprising or consisting of, p2-adrenergic, agonists, corticosteroids, nonsteroidal, anti-inflammatories, antibiotics, anticholinergic, antiviral, mucolytics, prostacyclin, beta-blocker, anti-infective, smoking cessation, angiotensin II receptor antagonists, anesthetic peptides and any combinations thereof.

Examples of bioactive compounds may be Formoterol, Formoterol fumarate inhalation solution, r-formoterol inhalation solution, Salbutamol, Salbutamol inhalation solution, (r-salbutamol) inhalation solution, Pirbuterol, Metaproterenol sulfate, Clenbuterol, Metaproterenol, Terbutaline, Salmeterol, Pirbuterol, Procaterol, Reproterol, Bitolterol, Fenoterol, Tulobuterol, atenolol, Salmeterol (r-salbutamol) Beclomethasone, Ciclesonide, Budesonide, Budesonide inhalation suspension, Fluticasone, Fluticasone inhalation suspension, Funisolide, Fluocotin butyl, Beclomethasone dipropionate, Triamcinolone acetonide, Beclomethasone/formoterol, Fluticasone/salmeterol, Ipratropium bromide/salbutamol, Fenoterol/ipratropium bromide, Cromolyn sodium, Tobramycin inhalation solution, Colistin inhalation solution, Aztreonam inhalation solution, Mometasone, Tobramycin, Pranlukast, Nedocromyl, amlexanox, Tiotropium bromide, Ipratropium bromide, enalaprilat, enalapril, Zanamivir, Ribavirin, Ipratropium bromide, Terbutaline Recombinant human DNase, Hypertonic saline inhalation solution, Sodium cromoglycate or N-acetyl cysteine, or any mixtures thereof.

Lloprost, metoprolol, propranolol, Pentamidine, Nicotine, losartan, Sevoflurane, Desflurane, Enflurane, Halothane, Isoflurane, or any mixtures thereof.

Examples of bioactive compounds are listed in table 1 below.

| Drug class | Bioactive compound |
|---|---|
| p2-adrenergic agonists | Formoterol, Formoterol fumarate inhalation solution, r-formoterol inhalation solution, Salbutamol, Salbutamol inhalation solution, (r-salbutamol) inhalation solution, Pirbuterol, Metaproterenol sulfate, Clenbuterol, Metaproterenol, Terbutaline, Salmeterol, Pirbuterol, Procaterol, Reproterol, Bitolterol, Fenoterol, Tulobuterol, atenolol |
| Corticosteroids | Salmeterol (r-salbutamol) Beclomethasone, Ciclesonide, Budesonide, Budesonide inhalation suspension, Fluticasone, Fluticasone inhalation suspension, Funisolide, Fluocotin butyl, Beclomethasone dipropionate, Triamcinolone acetonide |

| Drug class | Bioactive compound |
| --- | --- |
| Combinations | Beclomethasone/formoterol, Fluticasone/salmeterol, Ipratropium bromide/salbutamol, Fenoterol/ipratropium bromide |
| Nonsteroidal, anti-inflammatories, Antibiotics | Cromolyn sodium, Tobramycin inhalation solution, Colistin inhalation solution, Aztreonam inhalation solution, Mometasone, Tobramycin, Pranlukast, Nedocromyl, Amlexanox, |
| Anticholinergic | Tiotropium bromide, Ipratropium bromide, enalaprilat, enalapril, |
| antiviral | Zanamivir, Ribavirin, Ipratropium bromide, Terbutaline |
| Mucolytics | Recombinant human DNase, Hypertonic saline inhalation solution, Sodium cromoglycate, N-acetyl cysteine |
| Prostacyclin | Iloprost |
| Beta blocker | metoprolol, propranolol |
| Anti-infective | Pentamidine |
| Smoking cessation or other | Nicotine, losartan |
| Anesthetic | Sevoflurane, Desflurane, Enflurane, Halothane, Isoflurane |

The bioactive compound is selected from the group comprising or consisting of Gefitinib, Dasatinib, Imatinib, Bosutinib, Diclofenac (Sodium), Felodipine, Indapamide, Itraconazole and Quetiapine. The bioactive compound may be Clofazimine (NC009), OSU-03021 (NC023) and folic acid (NC026).

EXPERIMENTAL

Particle Manufacturing

A typical synthesis of nanoporous silica may be as following: Pluronic 123 (triblock co-polymer, EO20PO70EO20, Sigma-Aldrich) (4 g) as a templating agent and, 1,3,5-trimethylbenzene (TMB) (Mesitylene, Sigma-Aldrich) (3.3 g) as swelling agent were dissolved in 127 ml distilled $H_2O$ and 20 ml hydrochloric acid (HCl, 37%, Sigma-Aldrich) while stirring at room temperature (RT) for 3 days. The solution was preheated to 40° C. before adding 9.14 ml TEOS (Tetraethyl orthosilicate, Sigma-Aldrich). The mixture was stirred for another 10 mins at the speed of 500 rpm and then kept at 40° C. for 24 hours, then hydrothermally treated in the oven at 100° C. for another 24 hours. Finally, the mixture was filtered, washed and dried at room temperature. The product was calcined to remove the surfactant template and swelling agent. The calcination was conducted by heating to 600° C. with a heating rate of 1.5° C./min and kept at 600° C. for 6 hours followed by cooling to ambient conditions. The resulting product is a white powder comprising of porous silica particles.

Example of Particle Separation 100 g of raw nanoporous silica was fed into the air classifier, air flow adjusted from 53 to 42 m³/h and speed from 2475 to 13500 rpm, 11 g of the fines (particles with size below around 10% of the GSD) and 8 g of the coarse (particles with size above around 90% of the GSD) was collected. The particle size distribution $D_{90}/D_{10}$ was narrowed from 4.5 to 1.8.

Figure 2:
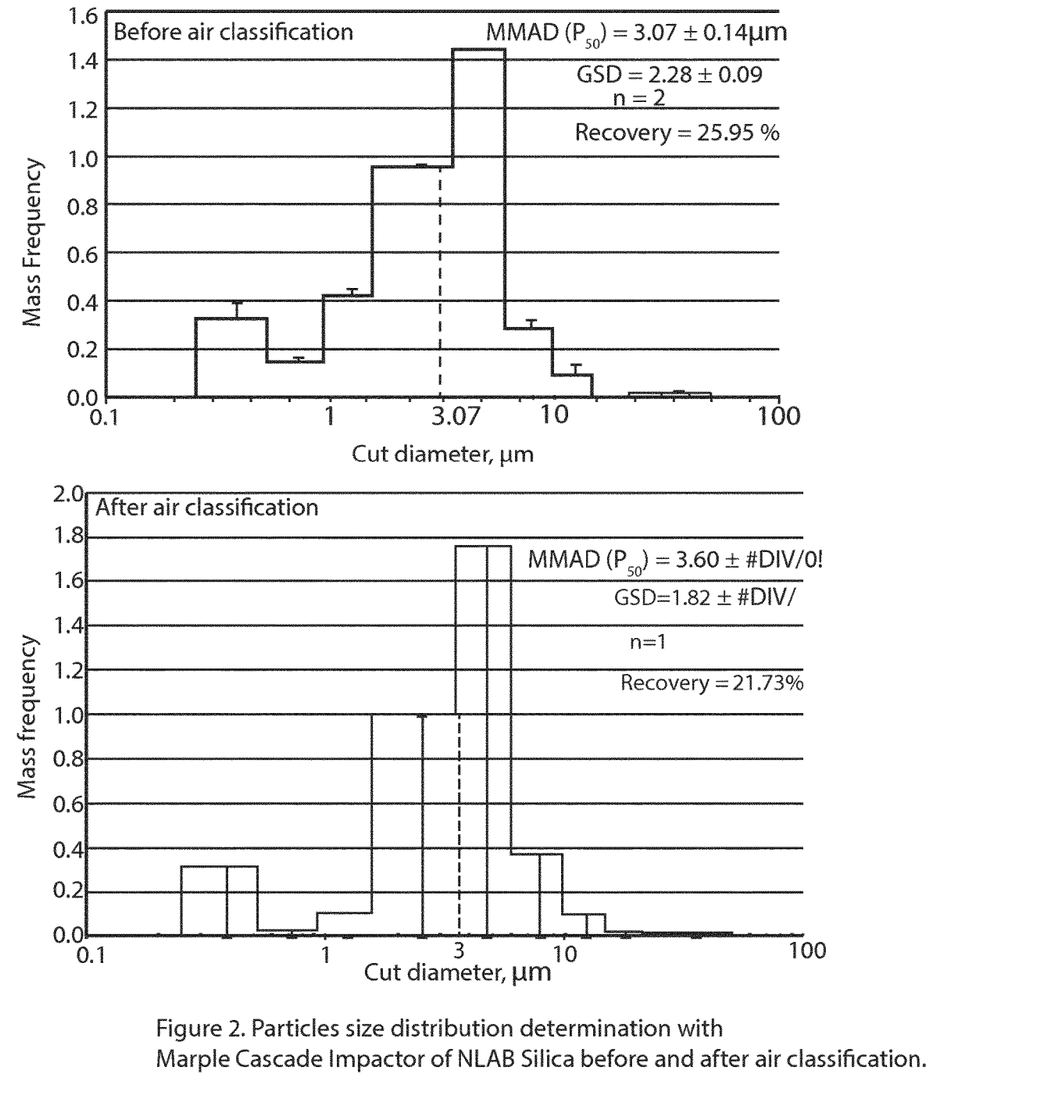

As shown in FIG. 2, the GSD was narrowed from 2.28 to 1.8 after air classification, which means that the geometric standard deviation (GSD) can be tailored by using the air classifier. FIG. 4 shows that the GSD of silica particles loaded with bioactive compound becomes narrower than the GSD of unloaded or naked silica particles.

Example of Drug Loading 2 g of nanoporous silica was added into 100 ml of concentrated methanol solution with 2 g of NLAB compound NCO26. The mixture was heated to 40° C. and stirred for 30 mins. The methanol was evaporated under vacuum. The loading concentration by mass was 50%.

Two bioactive compounds were also loaded in the same particles in sequence. Bioactive compounds NC009 and NC023 were successfully loaded into the silica particles. FIG. 3 shows the thermal gravimetric analysis (TGA) results, which indicate that both bioactive compounds are loaded in the porous silica particles.

EXAMPLES 1

100 mg NLAB-Silica particles were added to 500 ml simulated lung fluid (SLF), shaking under 37° C. with the shaking speed 100 rpm. The samples were taken in some time point and filtered. The concentration of Si was measured by Inductively Coupled Plasma—Atomic Emission Spectrometry (ICP—AES).

The samples in FIG. 7 with different particles size but similar pore structure were compared to check how particle size affects silica dissolution. It showed that the particles with 12 μm and 3 μm have the same dissolution kinetics with the similar porosity.

EXAMPLE 2

50 mg NLAB-Silica particles were added to 500 ml simulated lung fluid (SLF), shaking under 37° C. with the shaking speed 100 rpm. The samples were taken in some time point and filtered. The concentration of Si was measured by Inductively Coupled Plasma—Atomic Emission Spectrometry (ICP-AES).

FIG. 2 showed that different pore structure was the key parameter for the dissolution rate of silica in SLF. Silicon hydroxyl groups gave minor change on dissolution rate of silica in SLF. 95% of the silica can be fully dissolved within 24 hours.

EXAMPLE 3

5-20 mg loaded or unloaded particles were filled in one monodose inhaler, and then suction was done on simulated inhalation device. The capsule mass was weighed before and after suction to test remaining amount of particles sticking in the capsules. As shown in table 2, the particles coated by amino acid dramatically decreased the amount of particles remaining in the capsule.

TABLE 2

|  | Samples mass/mg | Remaining mass in capsule/mg | Remaining % |
|---|---|---|---|
| Loaded particles | 16.89 | 0.86 | 5 |
| Coating 5% glycine | 5.91 | 0.07 | 1.1 |
| Coating 5% Leucine | 5.67 | 0.08 | 1.4 |
| Coating 10% glycine | 10.2 | −0.045 | −0.4 |
| Coating 10% Leucine | 14.74 | 0.16 | 1 |

The present invention is not limited to the aspects disclosed but may be varied and modified within the scope of the following claims.

The invention claimed is:

1. A process for manufacturing loaded porous silica particles comprising at least one bioactive compound, comprising the steps of:
   a) providing silica particles, whereby the silica particles have a pore size between 1 and 100 nm, a pore volume between 0.1 and 3 cm$^3$/g and a surface area between 40 and 1200 m$^2$/g as measured by nitrogen adsorption isotherm and calculated using BET (Brunauer-Emmett-Teller) model to calculate the pore volume and pore size,
   b) separating the particles to obtain particles having a mass median aerodynamic diameter (MMAD) between 0.5 and 15 μm with a geometric standard deviation $(D_{84.1}/D_{15.9})^{1/2}$ (GSD) less than 2.5,
   c) loading the obtained particles with at least one bioactive compound, wherein the bioactive compound is a crystalline, or an amorphous or an oily compound, and optionally loading the particles with an additional bioactive compound.

2. The process according to claim 1, wherein the particles have an MMAD between 0.5 and 3.5 μm with a GSD less than 1.5.

3. The process according to claim 1, wherein the particles have an MMAD between 8 and 12 μm with a GSD less than 2.

4. The process according to claim 1, wherein the particles have a fine particle fraction (FPF) at least 60%.

5. The process according to claim 1, wherein the process comprises a further step of surface modifying the particles prior to separating or prior to loading.

6. The process according to claim 1, wherein the process comprises a further step of coating the particles after manufacturing or after loading.

7. The process according to claim 1, wherein silica particles are manufactured by a sol-gel method comprising a condensation reaction of a silica precursor solution with a non-miscible organic solution, oil, or liquid polymer in which droplets are formed by stirring or spraying the solution followed by gelation of the silica by means of change in pH and/or evaporation of the aqueous phase.

8. The process according to claim 1, wherein the silica particles are pseudo-spherical or cylindrical.

9. The process according to claim 1, wherein the silica particles have a pore size between 2 and 50 nm, a pore volume between 0.5 and 1.5 $cm^3/g$ and a surface area between 50 and 800 $m^2/g$ as measured by nitrogen adsorption isotherm and calculated using BET (Brunauer-Emmett-Teller) model to calculate the pore volume and pore size.

10. The process according to claim 1, wherein the particles are separated using an air classifier, or cyclonic separation, or elutriation, or sedimentation and/or sieving using one or more sieves.

11. The process according to claim 1, wherein the particles are loaded using solvent evaporation, impregnation, spray-drying, melting, supercritical $CO_2$ loading or freeze-drying.

12. The process according to claim 1, wherein the particles in step b) are separated to obtain particles having a mass median aerodynamic diameter (MMAD) between 0.5 and 5 μm with a geometric standard deviation $(D_{84.1}/D_{15.9})^{1/2}$ (GSD) less than 2.5.

13. The process according to claim 12, wherein the particles have an MMAD between 0.5 and 3.5 μm with a GSD less than 1.5.

14. The process according to claim 12, wherein the particles have a fine particle (FPF) at least 60%.

15. The process according to claim 12, wherein the bioactive compound is selected from the group comprising antiallergies, bronchodilators, pulmonary lung surfactants, analgesics, antibiotics, antiinfectives, leukotriene inhibitors or antagonists, antihistamines, antiinflammatories, antineoplastics, anticancer, anticholinergics, anesthetics, antituberculars, cardiovascular agents, enzymes, steroids, genetic material, viral vectors, antisense agents, proteins, peptides and combinations thereof.

16. The process according to claim 1, wherein the particles in step b) are separated to obtain particles having a mass median aerodynamic diameter (MMAD) between 5 and 15 μm with a geometric standard deviation $(D_{84.1}/D_{15.9})^{1/2}$ (GSD) less than 2.5.

17. The process according to claim 16, wherein the particles have an MMAD between 8 and 12 μm with a GSD less than 2.

18. The process according to claim 16, wherein the particles have a fine particle fraction (FPF) at least 60%.

19. The process according to claim 16, wherein the bioactive compound is selected from the group comprising antiallergies, bronchodilators, pulmonary lung surfactants, analgesics, antibodies, antiinfectives, leukotriene inhibitors or antagonists, antihistamines, antiinflammatories, antineoplastics, anticancer, anticholinergics, anesthetics, antituberculars, cardiovascular agents, enzymes, steroids, genetic material, viral vectors, antisense agents, proteins, peptides and combinations thereof.

* * * * *